United States Patent
Nogueiras Nieto et al.

(10) Patent No.: US 12,102,630 B2
(45) Date of Patent: Oct. 1, 2024

(54) CRYSTALLINE FORMS AND PROCESSES OF LENVATINIB BESYLATE

(71) Applicant: Synthon B.V., Nijmegen (NL)

(72) Inventors: Luis Nogueiras Nieto, Sant Boi de Llobregat (ES); Lisardo Alvarez Fernandez, Sant Boi de Llobregat (ES); Raymond Westheim, Nijmegen (NL); Katerina Jelinkova, Blansko (CZ)

(73) Assignee: Synthon B.V., Nijmegen (NL)

( * ) Notice: Subject to any disclaimer, the term of this patent is extended or adjusted under 35 U.S.C. 154(b) by 694 days.

(21) Appl. No.: 17/282,505

(22) PCT Filed: Oct. 1, 2019

(86) PCT No.: PCT/EP2019/076622
§ 371 (c)(1),
(2) Date: Apr. 2, 2021

(87) PCT Pub. No.: WO2020/070144
PCT Pub. Date: Apr. 9, 2020

(65) Prior Publication Data
US 2022/0062263 A1    Mar. 3, 2022

(30) Foreign Application Priority Data

Oct. 4, 2018 (EP) .................................... 18198662
May 2, 2019 (EP) .................................... 19172395

(51) Int. Cl.
*A61K 31/47*     (2006.01)
*A61K 9/48*      (2006.01)
*C07D 215/48*    (2006.01)

(52) U.S. Cl.
CPC .............. *A61K 31/47* (2013.01); *A61K 9/485* (2013.01); *A61K 9/4858* (2013.01); *A61K 9/4866* (2013.01); *C07D 215/48* (2013.01); *C07B 2200/13* (2013.01)

(58) Field of Classification Search
CPC ................................ A61K 31/47; A61K 9/484
See application file for complete search history.

(56) References Cited

U.S. PATENT DOCUMENTS 7,253,286 B2 *   8/2007   Funahashi ............ C07D 405/14
                                                    546/153

FOREIGN PATENT DOCUMENTS

| EP | 1698623 | | 12/2004 | |
|---|---|---|---|---|
| EP | 1698623 | A1 * | 9/2006 | ........... C07D 215/48 |
| EP | 1797881 | | 6/2007 | |
| EP | 1938842 | | 7/2008 | |
| EP | 2468281 | | 1/2016 | |
| WO | WO 2002/032872 | | 4/2002 | |
| WO | WO 2005/063713 | | 12/2007 | |
| WO | WO 2017/221214 | | 12/2017 | |

* cited by examiner

*Primary Examiner* — Andrew S Rosenthal
*Assistant Examiner* — Danielle Kim
(74) *Attorney, Agent, or Firm* — Buscher Patent PLLC

(57) ABSTRACT

The present invention relates to lenvatinib besylate, its crystalline forms and processes for making them. Furthermore, to a pharmaceutical composition comprising a therapeutically effective dose of lenvatinib besylate.

26 Claims, 5 Drawing Sheets

CRYSTALLINE FORMS AND PROCESSES OF LENVATINIB BESYLATE

BACKGROUND OF THE INVENTION

The present invention relates to crystalline forms of lenvatinib besylate and to pharmaceutical composition comprising lenvatinib besylate, having improved bioavailability.

Lenvatinib, 4-[3-chloro-4-(cyclopropylcarbamoylamino) phenoxy]-7-methoxy-quinoline-6-carboxamide of Formula (I),

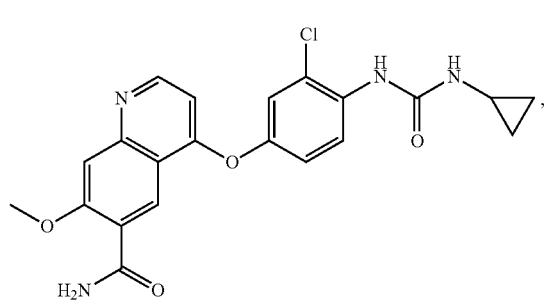

is a receptor tyrosine kinase (RTK) inhibitor that selectively inhibits the kinase activities of vascular endothelial growth factor (VEGF) receptors VEGFR1, VEGFR2 and VEGFR3.

Lenvatinib was first disclosed in WO2002/032872 by Eisai Co., Ltd. In WO2005/063713 several lenvatinib salts were disclosed including hydrochloride, hydrobromide, tosylate, sulphate, esylate and mesylate. Crystalline Forms A, B and C of lenvatinib mesylate and several mesylate (hydrated Form F, DMSO solvate, HAC-solvate Form I) and esylate solvates were described.

Methanesulfonic acid salt of lenvatinib, marketed by Eisai under the trade name Lenvima, is approved by EMA and FDA for the treatment of adult patients with progressive, locally advanced or metastatic, differentiated thyroid carcinoma, refractory to radioactive iodine. In Europe, lenvatinib mesylate marketed under the trade name Kisplyx, is also approved for the treatment of adult patients with advanced or unresectable hepatocellular carcinoma who have received no prior systemic therapy.

Lenvatinib as such has poor stability under humidifying and warm storage conditions. The marketed product comprises lenvatinib mesylate. It is known that the lenvatinib mesylate salt gelifies when in contact with dissolution media, this may cause a delay in its release. EP1797881 discloses a pharmaceutical composition that solved the above problems using an alkaline excipient with a pH of 8 a 5% w/w aqueous solution to reduce the degradation of the active substance and silicic acid to inhibit gelation. Sodium carbonates are described as suitable alkaline excipient.

EP2468281 discloses that when an alkaline earth metal carbonate is used as a base in combination with a disintegrant the pharmaceutical compositions have superior dissolution properties than other bases, even after long term storage. During prosecution the applicant provided results showing that when non earth metal carbonates such as sodium bicarbonate were used as stabilizers, the dissolution rate decreased after storage as compared to before storage and the dissolution time was additionally delayed.

It is desirable to provide an alternative pharmaceutically acceptable salt or the solvate of the salt that has usability as a medicament and there is still need of finding additional oral composition of lenvatinib which overcome the problems of gelation and degradation and is bioequivalent to the commercial lenvatinib mesylate capsules (Lenvima®).

DETAILED DESCRIPTION OF THE INVENTION

Different salts and their solid forms may exhibit different critical quality attributes such as dissolution and solubility behaviour, stability or hygroscopicity. Such variations may provide a basis for improving formulation, for example, by facilitating better processing or handling characteristics, improving the dissolution or physical and chemical stability and shelf-life.

The present invention provides the benzylsulfonic salt of lenvatinib and its solid forms that are useful in pharmaceutical compositions. Lenvatinib besylate can be prepared by dissolving or suspending the free base of lenvatinib in a suitable solvent together with benzylsulfonic acid preferably in 1:1 molar ratio. Solid forms of lenvatinib besylate can be anhydrous and/or non-solvated, they can also be in the form of hydrates and/or solvates.

In particular, in one of the embodiments of the present invention lenvatinib besylate maybe as crystalline Form 1 or crystalline Form 2 of lenvatinib besylate, which is a DMSO solvate.

The advantage of lenvatinib besylate in solid form is its improved physical and chemical stability, improved filterability and flow characteristics as well as dissolution rate and bioavailability. It has been determined that solid forms of lenvatinib besylate (in contrary to solid forms of marketed salt) don't tend to form a gel when in contact with water. Gelification limits the dissolution of API and can influence bioavailability of the drug.

In one of the embodiments of the present invention, lenvatinib besylate is in crystalline Form 1 which is an anhydrous crystalline form. It is characterized by XRPD pattern having 2θ values 4.9°, 11.2°, 17.10 and 24.6° (±0.2 degrees 2θ). The solid Form 1 can be further characterized by XRPD pattern having 2θ values 4.9°, 10.8°, 11.2°, 15.1°, 17.1°, 24.6° and 27.30 (±0.2 degrees 2θ). The crystalline Form 1 of lenvatinib besylate can be characterized by the reflections presented in Table 1.

TABLE 1

| Angle (2-Theta) | Intensity (%) | Angle (2-Theta) | Intensity (%) |
|---:|---:|---:|---:|
| 4.9 | 100.00 | 21.4 | 30.20 |
| 9.8 | 10.80 | 21.7 | 14.80 |
| 10.8 | 12.20 | 22.1 | 11.30 |
| 11.2 | 12.40 | 22.4 | 3.40 |
| 12.9 | 5.20 | 22.8 | 10.40 |
| 13.4 | 5.00 | 23.1 | 14.50 |

TABLE 1-continued

| Angle (2-Theta) | Intensity (%) | Angle (2-Theta) | Intensity (%) |
|---|---|---|---|
| 13.7 | 13.50 | 23.7 | 7.40 |
| 14.5 | 11.90 | 23.9 | 14.00 |
| 15.1 | 14.00 | 24.6 | 34.00 |
| 16.0 | 24.80 | 25.8 | 3.00 |
| 16.5 | 5.20 | 26.4 | 25.20 |
| 17.1 | 74.70 | 27.0 | 3.10 |
| 17.5 | 7.00 | 27.3 | 14.90 |
| 18.0 | 15.20 | 27.6 | 4.30 |
| 19.7 | 12.00 | 28.4 | 4.10 |
| 19.9 | 13.10 | 29.6 | 5.20 |
| 20.2 | 10.80 | 30.1 | 7.10 |
| 20.7 | 10.30 | 30.3 | 10.30 |
| 21.1 | 16.00 | 30.6 | 9.60 |

Figure 1:
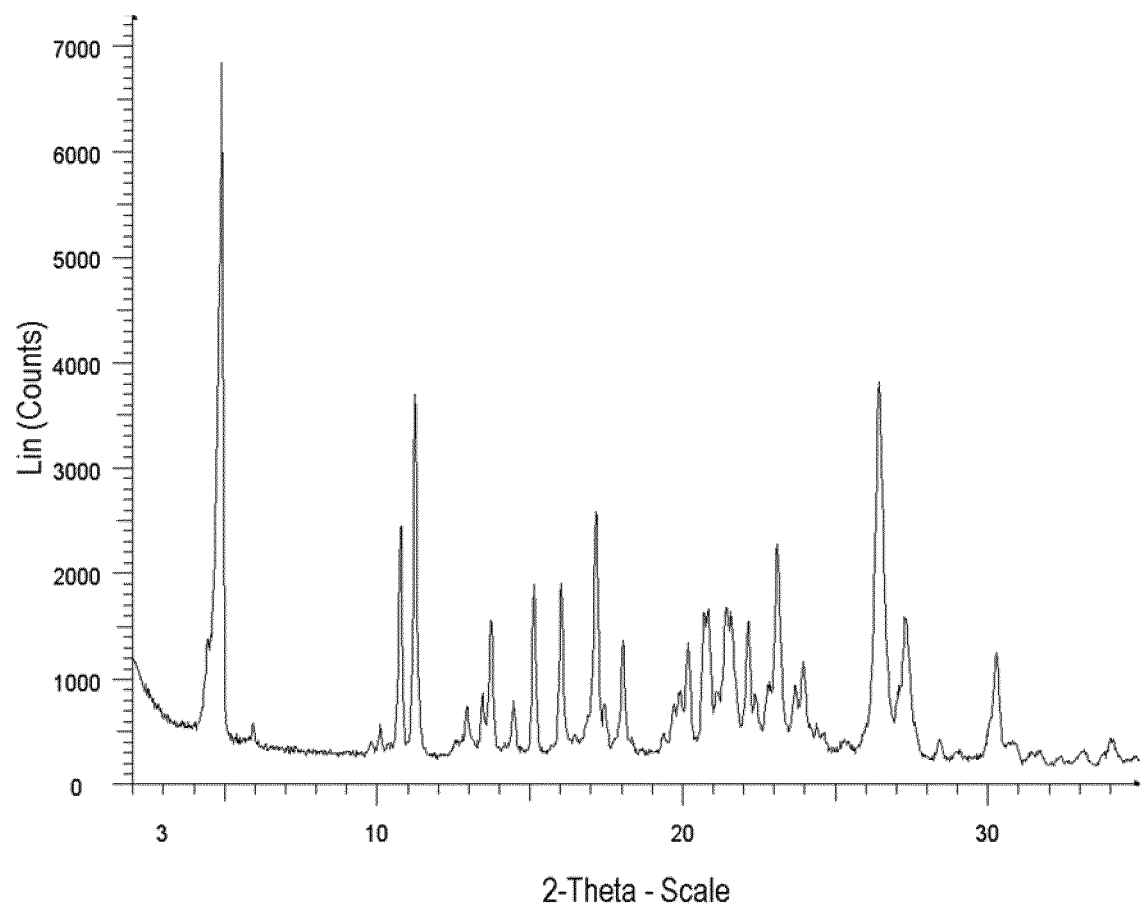
FIG. 1 shows XRPD pattern of crystalline Form 1 of lenvatinib besylate

The crystalline Form 1 can also be characterized by XRPD pattern depicted in FIG. 1. Form 1 of lenvatinib besylate can be further characterized by DSC pattern depicted in FIG. 2.

Crystalline Form 1 of lenvatinib besylate can be prepared by a process comprising following steps:
1. Suspending lenvatinib free base in $C_1$-$C_8$ alcohol and heating to reflux;
2. Adding benzenesulfonic acid;
3. Cooling and isolating the solid Form 1 of lenvatinib besylate.

The lenvatinib base used in forming lenvatinib besylate can be any form of lenvatinib base, including a hydrate or a solvate in any degree of purity. Alcohol used for suspending lenvatinib free base can be for example methanol, ethanol, propanol, butanol, pentanol, hexanol, heptanol or octanol. These can be used alone, or in admixture. The concentration of lenvatinib base in alcohol can be between 0.005 to 0.1 g/ml, preferably between 0.01 to 0.05 g/ml. The obtained solid can be isolated by any suitable technique, for example by filtration, and dried.

In another embodiment of the present invention, lenvatinib besylate is in crystalline Form 2 which is DMSO solvate. An attempt to prepare other solvates (DMF and DMA) of lenvatinib besylate resulted in obtaining low crystalline forms with only little amounts of solvents. Crystalline Form 2 is in contrast good crystalline form characterized by XRPD pattern 2θ values 16.2°, 19.4°, and 20.5° (±0.2 degrees 2θ). It can be further characterized by XRPD pattern having 2θ values 4.4°, 8.8°, 11.6°, 12.3°, 16.2°, 19.4°, 20.5° and 21.2° 25.8° (±0.2 degrees 2θ). The crystalline Form 2 of lenvatinib besylate can be characterized by the reflections presented in Table 2.

TABLE 2

| Angle (2-Theta) | Intensity (%) | Angle (2-Theta) | Intensity (%) |
|---|---|---|---|
| 4.4 | 22.00 | 21.5 | 26.60 |
| 4.9 | 100.00 | 22.2 | 24.60 |
| 5.9 | 9.30 | 22.4 | 13.40 |
| 9.8 | 6.30 | 22.9 | 15.40 |
| 10.1 | 9.00 | 23.1 | 36.20 |
| 10.8 | 39.00 | 23.7 | 14.90 |
| 11.3 | 59.10 | 24.0 | 18.60 |
| 12.6 | 6.60 | 24.4 | 9.20 |
| 13.0 | 11.80 | 24.6 | 7.70 |
| 13.5 | 13.80 | 25.4 | 6.70 |
| 13.7 | 24.70 | 26.5 | 60.90 |
| 14.5 | 12.60 | 27.3 | 25.30 |
| 15.1 | 30.20 | 28.5 | 6.60 |
| 16.0 | 30.40 | 29.1 | 5.20 |
| 16.5 | 7.40 | 30.3 | 19.90 |
| 17.2 | 41.20 | 30.8 | 6.00 |

TABLE 2-continued

| Angle (2-Theta) | Intensity (%) | Angle (2-Theta) | Intensity (%) |
|---|---|---|---|
| 17.5 | 12.00 | 31.5 | 4.80 |
| 18.1 | 21.80 | 31.7 | 5.10 |
| 19.4 | 7.50 | 32.4 | 4.00 |
| 19.7 | 12.00 | 33.2 | 5.10 |
| 19.9 | 14.10 | 33.8 | 4.90 |
| 20.2 | 21.40 | 34.1 | 6.60 |
| 20.8 | 25.00 | | |

Figure 3:
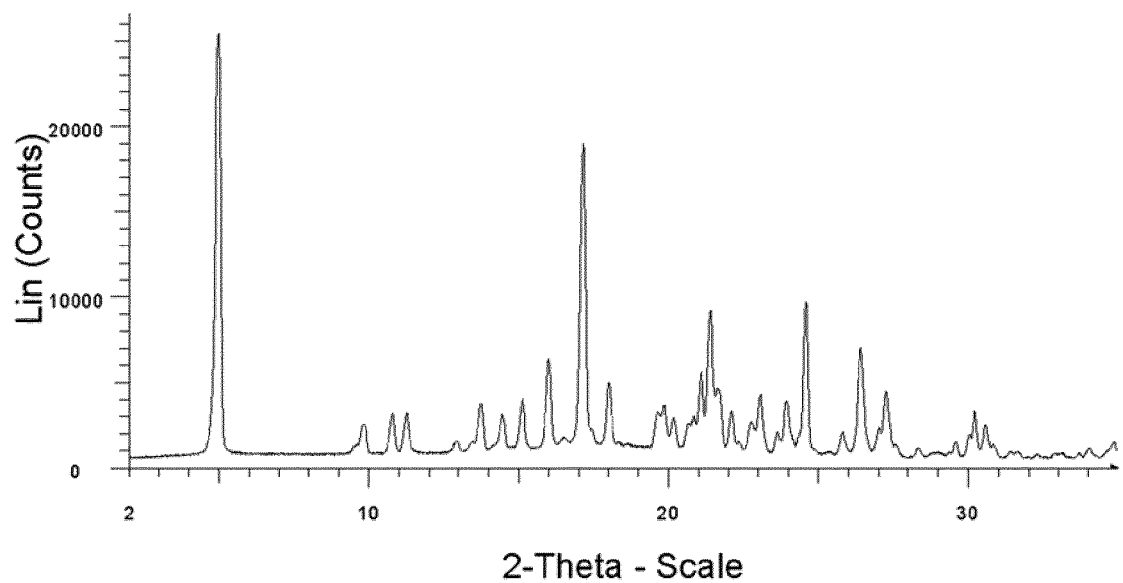
FIG. 3 shows XRPD pattern of crystalline Form 1 of lenvatinib besylate

The crystalline Form 2 can also be characterized by XRPD pattern depicted in FIG. 3. Form 2 of lenvatinib besylate can be further characterized by DSC pattern depicted in FIG. 4.

Crystalline Form 2 of lenvatinib besylate can be prepared by a process comprising following steps:
1. Dissolving lenvatinib free base in DMSO in elevated temperature;
2. Adding benzenesulfonic acid;
3. Cooling and isolating the solid Form 2 of lenvatinib besylate.

The lenvatinib free base used in forming lenvatinib besylate can be any form of lenvatinib base, including a hydrate or a solvate. The concentration of lenvatinib base in DMSO can be between 0.03 and 0.3 mg/ml. The elevated temperature means temperature between 35 to 160° C., more preferably between 50 to 110° C. The obtained solid can be isolated by any suitable technique, for example by filtration, and dried.

The variations in the procedures do not depart from the scope of the invention.

The solid Forms 1 or 2 of lenvatinib besylate can be processed into a suitable pharmaceutical composition.

A further aspect of the present invention relates to a pharmaceutical composition comprising a therapeutically effective dose of lenvatinib besylate. Pharmaceutical composition comprising lenvatinib besylate are stable and are bioequivalent to the commercial lenvatinib mesylate capsules (Lenvima®).

The pharmaceutical composition comprising the therapeutically effective dose of lenvatinib besylate may further comprise sodium carbonates in a weight ratio of lenvatinib besylate to sodium carbonates ranges from 1:1.5 to 1:10, more preferably from 1:2 to 1:7 most preferred ranges are from 1:3 to 1:5.

Sodium carbonates within this invention encompass sodium carbonate ($Na_2CO_3$), sodium bicarbonate ($NaHCO_3$), or mixtures of both, for instance effersoda which is sodium bicarbonate coated with sodium carbonate. A preferred carbonate within the invention is sodium bicarbonate.

In the acidic environment of the gastrointestinal tract, sodium carbonates produce $CO_2$:

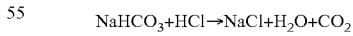

$$NaHCO_3 + HCl \rightarrow NaCl + H_2O + CO_2$$

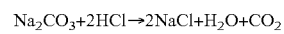

$$Na_2CO_3 + 2HCl \rightarrow 2NaCl + H_2O + CO_2$$

The $CO_2$ produced has a disintegrant effect that allows lenvatinib besylate to disperse in very small fine particles further avoiding gelation. The alkaline nature of the sodium carbonates prevents degradation and reduces impurity formation, including genotoxic impurities that may be formed upon hydrolysation of lenvatinib besylate. Moreover, the inventors have found that surprisingly, when the sodium carbonates are used in the ratio of the invention, the stability and the disintegration properties of these carbonates are such that lenvatinib besylate can be formulated without the addition of an extra disintegrant, as described in EP2468281. The addition of an extra disintegrant is optional and the skilled person could decide to add it.

Furthermore, sodium carbonates and specially $NaHCO_3$, have better solubility in water than the earth metal carbonates described in EP2468281 improving the pharmaceutical processability i.e. wet granulation with water.

The processability is improved in such a way that no binder is needed in such compositions. The addition of a binder is optional.

In one embodiment, the present invention relates to a pharmaceutical composition comprising a therapeutically effective dose of lenvatinib besylate having a particle size distribution $D_{90}$ from 5 to 50 μm, preferably from 8 to 25 μm, most preferred from 10 to 15 μm.

The $D_{90}$ value of the particle size distribution is defined as the particle diameter at which 90% by volume of the particles have a smaller diameter than the diameter which corresponds to the $D_{90}$ value measured by laser diffractometry. Specifically, a Malvern Instruments Mastersizer was used to determine the particle size distribution.

Besides sodium carbonates one or more pharmaceutically acceptable excipients can be used additionally in accordance with the present invention.

In a preferred embodiment sodium carbonates are used in an amount of 2% to 65%, preferably 5% to 55%, more preferably 20% to 50%, most preferably 25% to 50% by weight based on the total weight of the composition.

The one or more pharmaceutically acceptable excipients to be used additionally to sodium carbonates in accordance with the present invention can be chosen from, for example, diluents, binders, disintegrants, lubricants, and glidants.

In a preferred embodiment, lenvatinib besylate pharmaceutical composition can be mixed with pharmaceutically acceptable adjuvants, diluents or carriers.

Diluents are fillers which are used to increase the bulk volume of a tablet or capsule. By combining a diluent with the active pharmaceutical ingredient, the final product is given adequate weight and size to assist in production and handling. Binders hold the excipients that are present in a tablet/granule together.

The pharmaceutical composition of the present invention preferably contains at least one diluent.

Diluents are preferably used in an amount of from 15% to 75%, preferably 30% to 70%, more preferably 35% to 65%, even more preferably 35% to 55% by weight based on the total weight of the composition. Suitable examples of diluents to be used in accordance with the present invention include starch, pregelatinized starch, microcrystalline cellulose (MCC), mannitol, and calcium phosphate.

In a preferred embodiment of the present invention, the diluents to be used are mannitol, microcrystalline cellulose or mixtures thereof.

The pharmaceutical composition of the present invention may also contain a binder. Binders ensure that tablets and granules can be formed having the desired or required mechanical strength. Binders which are suitable for use in accordance with the present invention include povidone, hydroxypropyl cellulose, hydroxypropyl methylcellulose, and sodium carboxyl methylcellulose. Binders are preferably used in an amount of from 1% to 6% by weight based on the total weight of the composition.

The pharmaceutical composition of the present invention may also contain an extra disintegrant. Disintegrants are added to a tablet or capsule composition to promote the breakup of the tablet/capsule into smaller fragments in an aqueous environment, thereby increasing the available surface area and promoting a more rapid release of the active pharmaceutical ingredient. Suitable examples of disintegrants to be used in accordance with the present invention include crospovidone, L-HPC (Low substituted hydroxypropyl cellulose), sodium starch glycolate, croscarmellose sodium, and mixtures of any of the foregoing. Extra disintegrants preferably are used in an amount of from 1% to 25% by weight based on the total weight of the composition; the amount will depend on the tablet size and the chosen disintegrant. A preferred extra disintegrant is low substituted hydroxypropyl cellulose, in a preferred amount of from 15% to 25% by weight based on the total weight of the composition.

The pharmaceutical composition of the invention may also contain a lubricant. Lubricants are generally used in order to reduce sliding friction. In particular, to decrease the friction at the interface between the blend to be encapsulated and dosator of the encapsulation machine. Suitable lubricants to be used in accordance with the present invention include magnesium stearate, stearic acid, glyceryl behenate, hydrogenated vegetable oil, talc and glycerine fumarate. A preferred lubricant is talc. The pharmaceutical composition of the invention may also contain a glidant. Glidants enhance product flow by reducing interparticulate friction. A suitable example is colloidal silicon dioxide.

Lubricants and glidants preferably are used in a total amount of from 0.05% to 5% by weight based on the total weight of the composition, preferably from 1% to 5%.

In a preferred embodiment of the present invention, the amount of lenvatinib besylate in the composition depends on the condition and a patient to be treated. The pharmaceutical composition can be in the form of a solid oral composition, for example a capsule, a pill, a powder or a granule. In the solid oral composition, lenvatinib besylate can be mixed with one or more additives such as fillers or extenders or binders or wetting agents or disintegrating agents or absorbents or lubricants or buffering agents. The composition in a form of a tablet or a dragee or a capsule or a pill or a granule can be coated with a coating or shell such as enteric or other coating. The oral composition can be in a form of an oral emulsion or a solution or a suspension or a syrup. The composition can contain suitable additives such as diluent(s) or wetting agent(s) or emulsifying agent(s) or suspending agent(s) or sweetening agent(s) or flavouring agent(s). The examples of suitable additive(s) are known to those skilled in the art.

The suitable pharmaceutical composition can be in a parenteral form such as an injection or an infusion or an injectable depot or in a liposomal form comprising pharmaceutically acceptable aqueous or non-aqueous solution(s) or dispersion(s) or emulsions. The pharmaceutical composition can be also in a form of a powder for reconstitution into an injection or infusion. The composition can further comprise additives such as preservative(s) or wetting agent(s) or emulsifying agent(s) or dispersing agent(s) or antibacterial or antifungal agents. The examples of suitable additive(s) are known to those skilled in the art.

The suitable pharmaceutical composition can be in a form suitable for rectal or vaginal administration further comprising suitable additive(s). The examples of suitable additive(s) are known to those skilled in the art.

In a preferred embodiment, the pharmaceutical composition of the present invention, wherein the weight ratio of lenvatinib besylate to sodium carbonates ranges from 1:1.5 to 1:10 more preferably from 1:2 to 1:7 most preferred ranges are from 1:3 to 1:5, contains the following ingredients, based on the total weight of the composition:
  a. A therapeutically effective dose of lenvatinib besylate in an amount of from 4% to 30% by weight, preferably 4% to 25% by weight;
  b. Microcrystalline cellulose in an amount of from 10% to 65% by weight, 20% to 65% by weight, more preferably 25% to 55% by weight, even more preferably 27% to 45% by weight;
  c. Sodium carbonates, preferably sodium hydrogen carbonate, from 20% to 55% by weight, preferably from 20 to 50% by weight, more preferably 25% to 50% by weight;
  d. Optionally, Low substituted hydroxypropyl cellulose in an amount of from 15% to 25% by weight;
  e. Mannitol in an amount of from 7% to 18% by weight, preferably 5% to 10% by weight; and
  f. From 1% to 5% by weight of a lubricant and a glidants, preferably talc.

In one embodiment of the present invention, the therapeutically effective dose of lenvatinib is 4 mg, 10 mg, 18 mg and 24 mg.

The compositions of the present invention can be prepared by direct mixing or granulating the lenvatinib besylate with one or more pharmaceutically acceptable excipients, optionally followed by encapsulation, using equipment and methods well-known to the skilled artisan.

In a preferred embodiment the composition is prepared by granulation process.

Granulation can be performed by a wet or dry process. The wet granulation uses water or organic solvents or mixtures thereof as granulation liquid. The dry granulation can be performed by processes known as slugging and/or roller compaction.

The pharmaceutically acceptable excipients to be used in accordance with the present invention, can be used only intragranularly, only extragranularly, or both.

In a preferred embodiment the granules of the present invention are prepared by a wet-granulation process comprising the steps:
  a. Mixing lenvatinib besylate and sodium carbonates, preferably NaHCO$_3$, wherein the weight ratio of lenvatinib salt to sodium carbonates ranges from 1:1.5 to 1:10 most preferred ranges are from 1:3 to 1:5;
  b. Add one or more pharmaceutically acceptable excipients to form a mixture; c. Wet-granulating the resulting mixture;
  d. Further mixing the obtained granulate with one or more further pharmaceutically acceptable excipients to form a further mixture;
  e. Optionally encapsulating the granules.

The granules of the present invention typically have a particle size distribution D50 of from 200-350 µm, more preferably from 250 to 300 µm.

The present invention also relates to a pharmaceutical composition comprising granulates as described hereinabove in the form of a capsule or a tablet, preferably a capsule.

The pharmaceutical compositions described herein can be made using conventional methods and equipment well-known in the art.

The pharmaceutical compositions of the present invention show an in vitro dissolution profile wherein at least 80% of lenvatinib besylate is released at fifteen minutes when the composition is subjected to a dissolution study in 900 ml HCl 0.1N (pH 1) using a USP apparatus II at 50 rpm at 37° C. Preferably, at least 85% of lenvatinib besylate is released from the pharmaceutical composition at fifteen minutes. The pharmaceutical composition in accordance with the present invention is bioequivalent to the commercially available lenvatinib mesylate capsules.

The present invention is illustrated by the following Examples.

EXAMPLES

XRPD spectrum of crystalline Form 1 was obtained using the following measurement conditions:
Bruker D8;

| Setting | Value |
| --- | --- |
| 2θ range | 2-35° |
| Step size | 0.02° |
| Time per step | 1.5 s |
| Voltage | 40 kV |
| Focus slit | 0.2 mm |
| Divergence slit | v20.0 |
| Antiscatering slit | v20.0 |
| Secondary soller slit | 2.5° |
| Rotation speed | 30 rpm |

XRPD spectrum of crystalline Form 2 was obtained using the following measurement conditions:
Panalytical Empyrean diffractometer with Θ/2Θ geometry (transmition mode), equipped with a PixCell 3D detector:

| | |
| --- | --- |
| Start angle (2θ): | 2.0° |
| End angle (2θ): | 35.0° |
| Step size: | 0.026° |
| Scan speed: | 0.0955°/seconds |
| Radiation type: | Cu |
| Radiation wavelengths: | 1.5406Å (Kα1), primary monochromator used |
| Divergence slit: | 1/2° |
| Antiscatter slit: | 1/2° |
| Soller slit: | 0.02 rad |
| Detector slit: | 7.5 mm |
| Rotation speed: | 30 rpm |

DCS patterns were obtained using the following conditions: 10° C./min –> 250° C.

Example 1: Crystalline Form 1 of Lenvatinib Besylate

Lenvatinib free base in the quantity of 0.5 g was suspended in 10 ml ethanol. The mixture was stirred and heated to reflux (80° C.). Benzenesulfonic acid (1 eq.) was added to the suspension and reflux was maintained for about 10 minutes. An additional 20 ml of ethanol was added to the suspension. The mixture was slowly cooled to 25° C. and stirred for about 20 hrs. The solid was filtered and dried at 25° C. for 24 hrs.

Figure 2:
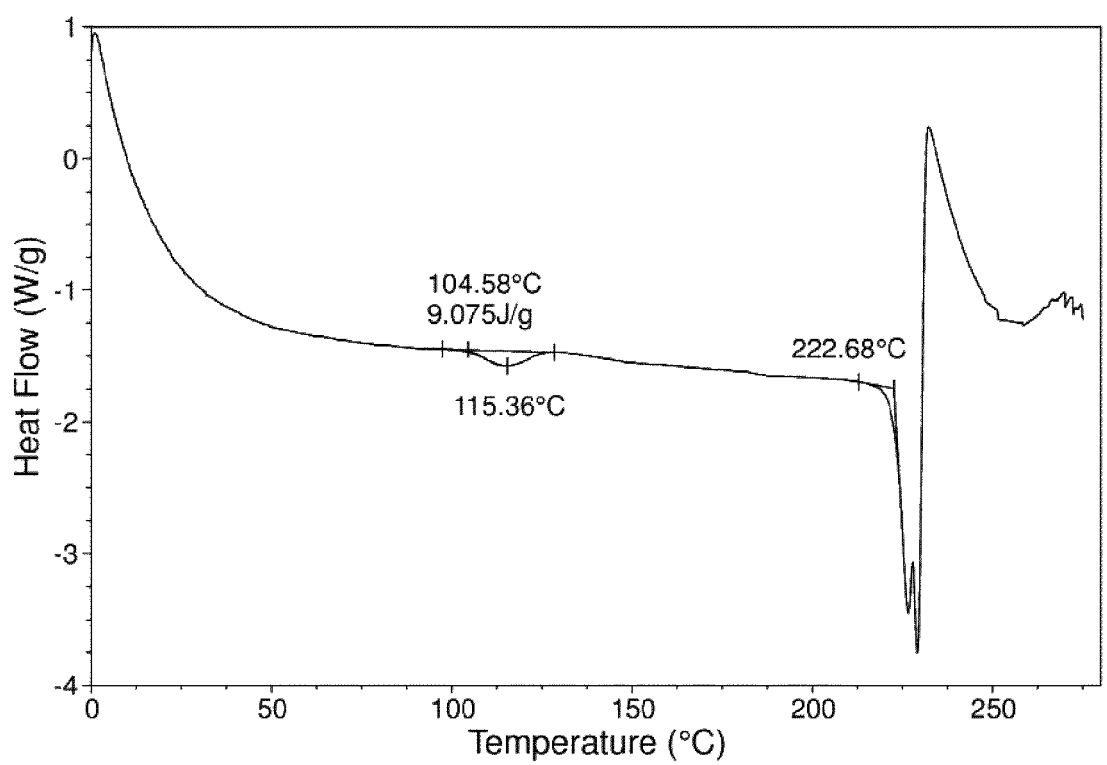
FIG. 2 shows DSC pattern of crystalline Form 1 of lenvatinib besylate

XRPD pattern of obtained solid is depicted in FIG. 1 and DSC pattern of obtained solid is depicted in FIG. 2.

Example 2: Crystalline Form 1 of Lenvatinib Besylate

Lenvatinib free base in the quantity of 2.73 g was suspended in 175 ml methanol. The mixture was stirred and heated to reflux (67° C.). About 1.2 g of benzenesulfonic acid in 10 ml methanol was added to the suspension and reflux was maintained for about 1 to 1.25 hours. The mixture was slowly cooled to about 25° C. and stirred for about 20.5 hours. The suspension was filtered over a P3-glass filter. The solid was washed with methanol and air-dried at room temperature.

XRPD pattern of obtained solid is depicted in FIG. 3.

Example 3: Crystalline Form 2 of Lenvatinib Besylate

Lenvatinib free base in the quantity of 0.5 g was dissolved in 4 ml of DMSO at 65° C. 0.185 g of benzenesulfonic acid in 0.5 ml of DMSO was added to the suspension. Solid was observed after 10 minutes. The mixture was spontaneously cooled to 25° C. and stirred for 1 hour. Then solid was filtered and dried under vacuum at 30° C. for 24 hours.

Figure 4:
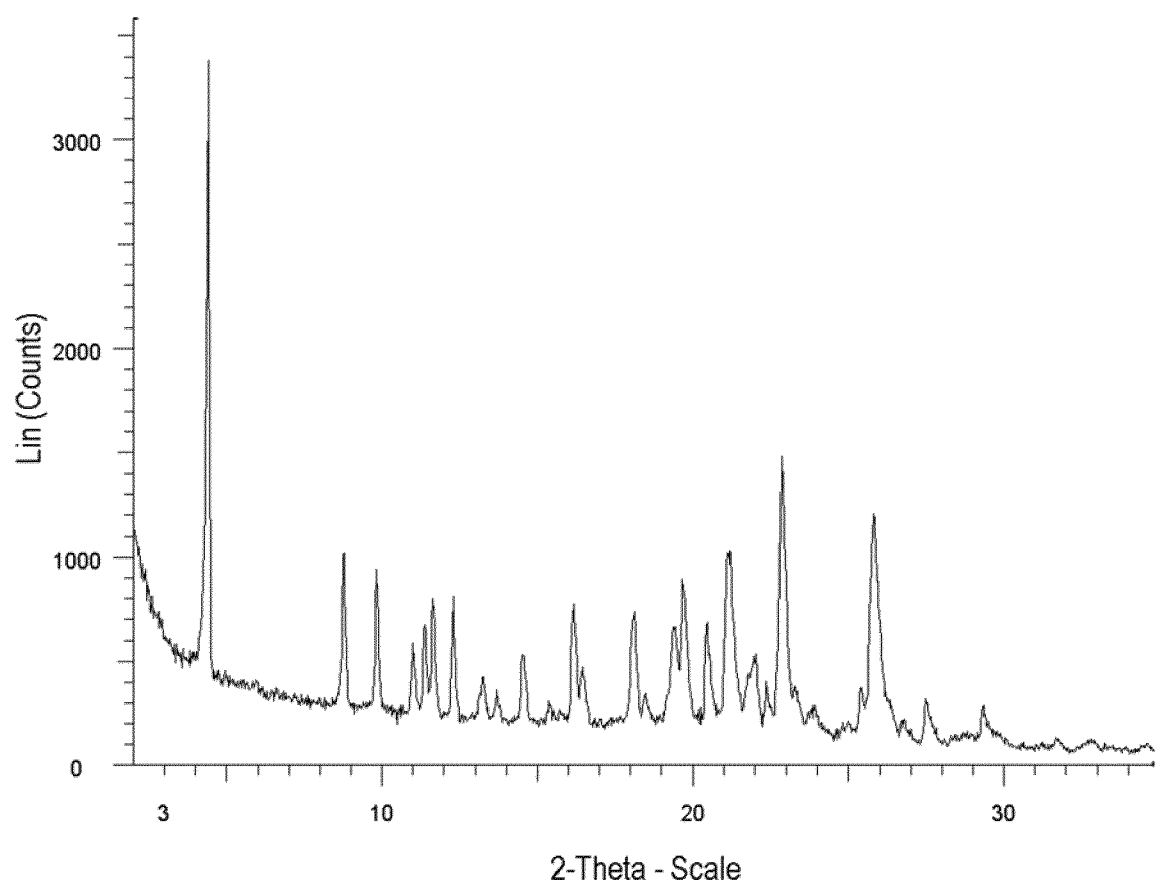
FIG. 4 shows XRPD pattern of crystalline Form 2 of lenvatinib besylate
Figure 5:
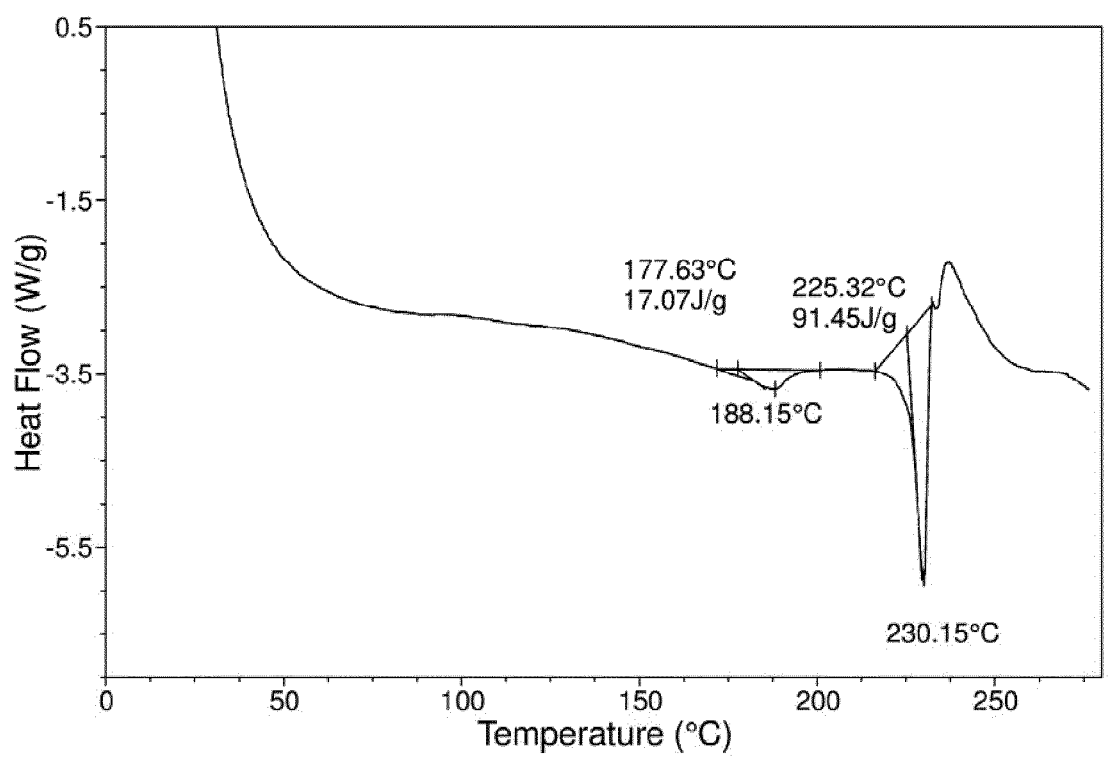
FIG. 5 shows DSC pattern of crystalline Form 2 of lenvatinib besylate

XRPD pattern of obtained solid is depicted in FIG. 4 and DSC pattern of obtained solid is depicted in FIG. 5.

Example 4

TABLE 1

Pharmaceutical composition of formulation A.
Formulation A

| Components | mg/capsule | % |
|---|---|---|
| Lenvatinib besylate | 13.71 | 13.71% |
| Sodium hydrogen carbonate | 33.00 | 33.00% |
| Mannitol | 8.75 | 8.75% |
| Microcrystalline cellulose | 41.54 | 41.54% |
| Talc | 3.00 | 3.00% |
| Total weight | 100.00 | 100.00% |

5.48 grams of lenvatinib besylate, 13.2 grams of sodium hydrogen carbonate, 3.50 grams of mannitol and 16.62 grams of microcrystalline cellulose were weighted and sieved through a 0.8 mm mesh for the deagglomeration of the materials and then mixed for 10 minutes at 72 rpm resulting in a homogenous blend (1). 1.20 grams of talc were weighted and sieved through 0.5 mm and then mixed with the previous blend (1) for 3 minutes at 72 rpm resulting in a homogenous blend (2). The resulting blend (2) was then encapsulated into hypromellose hard capsules size 4.

The invention claimed is:

1. A lenvatinib besylate salt.

2. The lenvatinib besylate according to claim 1 in solid form.

3. The lenvatinib besylate according to claim 2 in crystalline form.

4. The lenvatinib besylate according to claim 3 in crystalline Form 1 characterized by XRPD powder diffraction pattern comprising the peaks at about 4.9°, 11.2°, 17.10 and 24.6° degrees 2θ (±0.2 degrees 2θ).

5. The lenvatinib besylate according to claim 3 in crystalline Form 1 characterized by XRPD powder diffraction pattern of FIG. 1.

6. The lenvatinib besylate according to claim 3 in crystalline Form 1 characterized by DSC pattern depicted in FIG. 2.

7. The lenvatinib besylate according to claim 3 in crystalline Form 2 characterized by XRPD powder diffraction pattern comprising the peaks at about 16.2°, 19.4°, 20.5° degrees 2θ (±0.2 degrees 2θ).

8. The lenvatinib besylate according to claim 3 in crystalline Form 2 characterized by XRPD powder diffraction pattern of FIG. 4.

9. The lenvatinib besylate according to claim 3 in crystalline Form 2 characterized by DSC pattern depicted in FIG. 5.

10. A process for preparation of lenvatinib besylate crystalline Form 1, comprising suspending lenvatinib free base with benzenesulfonic acid in $C_1$-$C_8$ alcohol and isolating the crystalline Form 1 of lenvatinib besylate characterized by XRPD powder diffraction pattern comprising the peaks at about 4.9°, 11.2°, 17.10 and 24.6° degrees 2θ (±0.2 degrees 2θ).

11. The process according to claim 10 wherein the $C_1$-$C_8$ alcohol is selected from methanol, ethanol, propanol, butanol, pentanol, hexanol, heptanol and octanol or mixtures thereof.

12. The process according to claim 11 wherein the $C_1$-$C_8$ alcohol is methanol or ethanol.

13. A process for preparation of lenvatinib besylate crystalline Form 2, comprising dissolving lenvatinib free base in DMSO at elevated temperature, adding benzenesulfonic acid, cooling the mixture and isolating the crystalline Form 2 of lenvatinib besylate characterized by XRPD powder diffraction pattern comprising the peaks at about 16.2°, 19.4°, 20.5° degrees 2θ (±0.2 degrees 2θ).

14. A pharmaceutical composition comprising a therapeutically effective dose of lenvatinib besylate according to claim 1.

15. The pharmaceutical composition according to claim 14 further comprising sodium carbonates having a weight ratio of lenvatinib besylate to sodium carbonates in a range from 1:1.5 to 1:10.

16. The pharmaceutical composition according to claim 15 wherein the weight ratio of lenvatinib besylate to sodium carbonates ranges from 1:3 to 1:5.

17. The pharmaceutical composition according to claim 15 wherein sodium carbonates are present in a range from 20% to 55%, by weight based on the total weight of the composition.

18. The pharmaceutical composition according to claim 15 wherein the sodium carbonates is sodium bicarbonate.

19. The pharmaceutical composition according to claim 14, wherein the composition further comprises:
   a) At least one diluent in an amount of from 15% to 75% by weight based on the total weight of the composition;
   b) Optionally, disintegrant in an amount of from 1% to 25% by weight based on the total weight of the composition; and
   c) Lubricant in an amount of from 1% to 5% by weight based on the total weight of the composition.

20. The pharmaceutical composition according to claim 19 wherein the diluent is present in an amount of from 35% to 65% by weight based on the total weight of the composition.

21. The pharmaceutical composition according to claim 19 wherein the diluent is MCC, mannitol or a mixture of both.

22. The pharmaceutical composition according to claim 14 comprising, based on the total weight of the composition:
   a) A therapeutically effective dose of lenvatinib besylate in an amount of from 4% to 25% by weight;
   b) Microcrystalline cellulose in an amount of from 20% to 65% by weight;
   c) Sodium carbonates, in an amount of from 20% to 50%, preferably 20% to 55% by weight;
   d) Optionally, low substituted hydroxypropyl cellulose in an amount of from 15% to 25% by weight;
   e) Mannitol in an amount of from 7% to 18%; and
   f) Talc in an amount of from 1% to 5% by weight.

23. The pharmaceutical composition according to claim 15 prepared by wet granulation process.

24. The pharmaceutical composition according to claim 15 prepared by direct mix.

25. The pharmaceutical composition according to claim 23, which process comprises:
  a. Mixing lenvatinib besylate and sodium carbonates wherein the weight ratio of lenvatinib besylate to sodium carbonates ranges from 1:1.5 to 1:10;
  b. Add one or more pharmaceutically acceptable excipients to form a mixture;
  c. Wet-granulating the resulting mixture;
  d. Further mixing the obtained granulate with one or more further pharmaceutically acceptable excipients to form a further mixture;
  e. Optionally encapsulating the granules.

26. The pharmaceutical composition according to claim 14 in the form of a capsule.

\* \* \* \* \*